(12) United States Patent
Walker et al.

(10) Patent No.: US 8,200,505 B2
(45) Date of Patent: Jun. 12, 2012

(54) SYSTEM AND METHOD FOR CREATING AND RENDERING DICOM STRUCTURED CLINICAL REPORTING VIA THE INTERNET

(75) Inventors: Craig Allan Walker, Greenville, SC (US); Michal Kostrzewa, Warsaw (PL); Steven Devann Johnson, Greenville, SC (US)

(73) Assignee: Vidistar L.L.C., Greenville, SC (US)

( * ) Notice: Subject to any disclaimer, the term of this patent is extended or adjusted under 35 U.S.C. 154(b) by 0 days.

(21) Appl. No.: 12/932,973

(22) Filed: Mar. 10, 2011

(65) Prior Publication Data

US 2011/0166885 A1    Jul. 7, 2011

Related U.S. Application Data

(63) Continuation of application No. 11/592,608, filed on Nov. 3, 2006, now abandoned.

(51) Int. Cl.
*G06Q 10/00* (2006.01)
*G06Q 50/00* (2012.01)

(52) U.S. Cl. .................................. 705/2; 705/3
(58) Field of Classification Search .................. 705/2–4
See application file for complete search history.

(56) References Cited

U.S. PATENT DOCUMENTS

| | | | | |
|---|---|---|---|---|
| 6,643,641 | B1* | 11/2003 | Snyder | 707/709 |
| 7,283,857 | B1* | 10/2007 | Fallon et al. | 600/407 |
| 2002/0143727 | A1* | 10/2002 | Hu et al. | 707/1 |
| 2003/0187689 | A1* | 10/2003 | Barnes et al. | 705/2 |
| 2004/0083217 | A1* | 4/2004 | Brackett et al. | 707/100 |
| 2004/0165700 | A1* | 8/2004 | Batchelder et al. | 378/146 |
| 2004/0252871 | A1* | 12/2004 | Tecotzky et al. | 382/128 |
| 2005/0149536 | A1* | 7/2005 | Wildes et al. | 707/100 |
| 2005/0273365 | A1* | 12/2005 | Baumgartner et al. | 705/3 |
| 2006/0004745 | A1* | 1/2006 | Kuhn et al. | 707/4 |
| 2006/0282447 | A1* | 12/2006 | Hollebeek | 707/101 |
| 2006/0285753 | A1* | 12/2006 | Yamasaki | 382/209 |
| 2007/0025606 | A1* | 2/2007 | Gholap et al. | 382/128 |
| 2007/0078674 | A1* | 4/2007 | Weinberg et al. | 705/1 |
| 2008/0109250 | A1* | 5/2008 | Walker et al. | 705/2 |

OTHER PUBLICATIONS

Tachibana et al., "Design and Development of a Secure DICOM-Network Attached Server" Jpn J Radiol Technol 62(4) 2006.*
Hussein et al., "DICOM Structured Reporting—Part 2. Problesm and Challenges in Implementation for PACS Workstations." InfoRAS 897 RSNA, 2004.*
VidiStar, "Presenting . . . VidiStar's Standalone Viewer" 2004.*
Kalet et al., "A declarative implentation of the DICOM-3 network protocol" Journal of Biomedical Informatics 36 (2003) 159-176.*

* cited by examiner

*Primary Examiner* — Neal Sereboff
(74) *Attorney, Agent, or Firm* — The Matthews Firm (57) ABSTRACT

Methods for implementing a structured clinical reporting system employing a DICOM Structured Reporting (SR) software database engine that maps clinical report data into a clinical structured reporting data format are disclosed. A workstation is used to create, sign, render, or transmit a structured clinical report. A conversion engine performs image recognition on the structured clinical report, which includes identifying data therein, segmenting the report, using a library to perform value object extraction on the segments, and converting the value objects to a DICOM format. A PACS server is usable to communicate with the conversion engine, workstation, and database. Various software plug-ins are usable, such that different methods of acquiring user input may be implemented.

17 Claims, 9 Drawing Sheets

SYSTEM AND METHOD FOR CREATING AND RENDERING DICOM STRUCTURED CLINICAL REPORTING VIA THE INTERNET

CROSS REFERENCE TO RELATED APPLICATIONS

The present application is a continuation application which claims priority to and the benefit of the U.S. patent application having the Ser. No. 11/592,608, filed Nov. 3, 2006 now abandoned, the entirety of which is incorporated herein by reference.

FIELD OF THE INVENTION

The present invention relates, generally, to a system and method of creating and rendering structured clinical reports over the Internet. Specific embodiments of the present invention relate to a system and method for creating and rendering structured clinical reports, such as DICOM Structured Reports (DSR), using a Transmission Control Protocol/Internet Protocol (TCP/IP) for connecting computers to the Internet. TCP/IP is the basic communication protocol for the Internet. The present invention can allow users, such as health care providers, to access diagnostic information and render clinical reports using a computer that is connected to the Internet, or world wide web, through an encrypted connection, and permit the users to view clinical and diagnostic patient information over a wide area network (WAN) using a secure connection over the Internet from any computer. Embodiments of the present invention can use any computer and do not require a traditional, designated clinical workstation. Traditional clinical workstations are for exclusive purposes and have limitations. Further, traditional clinical workstations and related information systems are precluded from rendering clinical structured reports over the Internet and enabling such systems and methods.

NOTICE OF COPYRIGHT

A portion of the disclosure of this patent document contains material subject to copyright protection. The owner of the copyright authorizes the reproduction of the work of authorship in the patent document or the patent disclosure, as it appears in the Patent and Trademark Office file or records, but otherwise reserves all copyright protections and rights whatsoever.

BACKGROUND OF THE INVENTION

With technological advances in modern medicine, the digital transformation of diagnostic data for medical interpretation and analysis has heightened the focus on clinical quality, standardization and efficiency. In the 1990s, the Digital Imaging and Communications in Medicine (DICOM) standards were published by the American College of Radiology and the National Electronic Manufacturers Association in order to outline the data format, flow, and hierarchy of electronic information of diagnostic images and related information between computer systems over TCP/IP networks. With the advances in digital imaging and the transfer of this information over TCP/IP networks, medical professions, such as cardiology, have begun to adopt standardized clinical reports that outline the basic content for medical interpretation and analysis. Organizations like the American Society of Echocardiography (ASE) and the DICOM Standards Committee have developed a uniform structure and set of codes for the transfer of echocardiography reporting information (DICOM Supplement 72, Echocardiography Procedure Reports, Jun. 23, 2003). The outcome of these organization's advancements pertaining to standardizing the transfer of clinical information is the result of historical frustration to effectively share data between proprietary information systems and DICOM imaging modalities (for example, ultrasound machines, X-ray machines, CT scan devices, nuclear imaging devices, etc.), such as not being able to communicate and transfer common measurements and information for clinical use. In many fields including medicine, veterinary medicine, and scientific manufacturing and investigation, it is necessary to render a report based on professional subjective interpretation. Due to the amount of variance resulting in personal opinion, these reports may differ greatly within the same profession. As a consequence to the variability in interpretation, organizations are establishing standardized approaches for the creation of interpretive reports. In medicine, these reports prove vital in the legal, professional diagnostic analysis, and medical interpretation of the patient's condition, and can further provide a basis for future assessments and ongoing treatments. Whether in the hospital setting, clinical setting, physician practice, or health service setting, clinical reporting provides a legal, confidential record of a clinician's assessment of a patient's condition.

Typically, a clinical report consists of basic clinical information related to the patient's exam including but not limited to patient demographic information, date & time of the study, performing examiner's name, interpreting physician name (s), reimbursement code(s), study quality, clinical assessment, medical findings, diagnostic measurements, diagnostic data, vital information, diagrams, and impressions. Contemporary methods for creating clinical reports includes performing a diagnostic exam on a patient, whereby a physician reviews the diagnostic information, such as digital ultrasound, and either manually documents the clinical findings and diagnostic impression, or the physician dictates this basic clinical information into a recording device, such as a Dictaphone, where it is later transcribed into a document format that becomes part of the patient's permanent chart. These methods either delay the report processing time or limit the physician to using only designated workstations solely for this purpose. These reporting methods often result in furthering the variability in producing accurate reports, limit the workflow, are inefficient, or are not cost effective. To confound the variability in clinical reporting, DICOM modalities often utilized proprietary coding schemas for labeling the clinical information, which results in complicating, if not comprising, the integration of this data with additional information systems used by medical professionals.

It is also important that clinical information be held confidential and secure from unauthorized use. The Health Insurance Portability and Accountability Act (HIPAA) authorized medical professionals to protect the confidentiality of patients' medical records, such as clinical reports. The impact of HIPAA instituted a duty on medical professionals to comply with these governmental standards of conduct by requiring the secure transfer of patient data/information using secure TCP/IP network encryption technology, like Secure Socket Layer (SSL) encryption or Virtual Private Network (VPN) techniques over public communication networks. Public networks provide a cost-effective communication option to accessing information and data over the Internet, or world-wide-web. Using TCP/IP communication protocol and encryption, like SSL or VPN, medical professionals can access clinical information, such as DICOM data, images, media, etc. over the Internet. However, while the Internet provides medical professionals access to this information over the public communications network, traditional imaging modalities along with their software architectures do not enable medical professionals to remotely render a clinical structured report, particularly in a DICOM Structured Report format.

As a result, physicians have turned to utilizing technological innovations that depict digital diagnostic images in place of analog systems or static radiological imagery. While these formats for medical interpretation are growing in medical application, these systems and methods rely on utilizing local area networks for communicating, transmitting, and processing the digital data and medical media between computers. With the expansion of health systems and the growth in competition between physicians and hospitals over reimbursement, physicians have begun to incorporate Picture Archiving and Communications System (PACS) into their workplace for the storage and retrieval of medical images and video. While these systems are expanding in the marketplace, most clinical reporting technologies are limited to local area networks and do not enable the remote rendering of clinical structured reports over the Internet.

Many inventors have attempted to solve these problems by allowing the medical professionals to only view a completed clinical report over the Internet using a VPN or SSL connection; these methods do not permit the user to create and render a DICOM Structured Report format of a clinical report over the Internet. One such method is to provide the local viewing of diagnostic digital images and video clips and report rendered over a local area network whereby the user operates a viewer, such as a DICOM viewer, and a reporting software system; however in this method, the user generates and renders a report that is limited to only the LAN network architecture and not the Internet.

Moreover, traditional DICOM imaging modalities store DICOM data in proprietary formats which often require optical character recognition (OCR) for capturing and populating measurements into reports. These software applications perform "screen scrubbing" of the DICOM image bitmap that contains the measurements from the static image or image worksheet and populate the data into a database system, such as Microsoft Excel and Microsoft Access. On the other hand, new contemporary DICOM modalities, such as the Philips HD11 ultrasound system, Philips IE33, and the GE Vivid 7, now transmit the DICOM data in a DICOM Structured Report (DSR) format based on the DICOM Supplement 72 structure and format for transmitting ultrasound data and information (example, measurements). However, these technologies employ DICOM SR standard for procedure reports only, and do not take an advantage of DSR for creating diagnostic reports. They do not enable a user to render DSR clinical reports, build new DSR report templates (example, transthoracic echocardiography report, obstetrical report, etc.), store data obtained from OCR data into the DSR format, or alter (customize) the graphical user interface (GUI) for creating and amending DICOM structured reports. Additionally, contemporary inventions do not combine web-viewing of DICOM data and DICOM Structured Reports where the DICOM viewer uses the "Web Access to Data Objects" (WADO) protocol, which is the DICOM standard way to access images through an Internet browser via HyperText Transfer Protocol (HTTP), the underlying protocol used by the World Wide Web (HTTP defines how messages are formatted and transmitted, and what actions Web severs and browsers should take in response to various commands).

In lieu of the technological shortcomings of these various currently 170 available systems, there is still a need for an Internet-based software for rendering structured reports, particularly DSR, in an efficient, timely manner with an easy-to-use graphical user interface. Specifically, there is a desire for a system and method for creating and rendering clinical structured reports over the Internet using an encrypted, SSL connection in accordance with DICOM standards.

It is, therefore, a feature of the present invention to provide a system and method of creating and rendering structured clinical reports over the Internet.

Additional features and advantages of the invention will be set forth in part in the description which follows, and in part will become apparent from the description, or may be learned by practice of the invention. The features and advantages of the invention may be realized by means of the combinations and steps particularly pointed out in the appended claims.

SUMMARY OF THE INVENTION

To achieve the foregoing objects, features, and advantages and in accordance with the purpose of the invention as embodied and broadly described herein, a method for implementing a structured clinical reporting system over the Internet is provided. The structured clinical report having a DICOM Structured Reporting format and the Internet is adapted to work in conjunction with Hypertext transfer protocol (HTTP) for connecting a server and multiple workstations via the Internet. The method comprising the steps of providing communication between a workstation and the server via the Internet. Adapting a reporting system to have a reporting engine in operative communication with the workstation, an image viewer-editor and the server. Providing a workstation for creating the clinical reports, signing the clinical reports, rendering the clinical reports, and transmitting the clinical reports to and from the PACS server over the Internet. The workstation having the capability to manipulate a study list stored on the server. Also, a picture archiving and communications system (PACS) server is provided. Providing communication between the PACS server and a database server, and providing communication between the PACS server and a viewer and the workstation over HTTP protocol. Providing communication between the PACS server and the imaging modalities using a DICOM interface, such that the PACS server is in operative communication with the imaging modalities over a DICOM protocol and is in operative communication with the database. The workstation encompassing an interface viewer comprising the reporting engine, the image viewer-editor and the study list viewer is in operative communication with the PACS server via the Internet using the HTTP protocol.

BRIEF DESCRIPTION OF THE DRAWINGS

The accompanying drawings, which are incorporated in and constitute a part of the specification, illustrate a preferred embodiment of the invention and together with the general description of the invention given above and the detailed description of the preferred embodiment given below, serve to explain the principles of the invention.

The above general description and the following detailed description are merely illustrative of the generic invention, and additional modes, advantages, and particulars of this invention will be readily suggested to those skilled in the art without departing from the spirit and scope of the invention.

DETAILED DESCRIPTION OF THE PREFERRED EMBODIMENTS

Reference will now be made in detail to the present preferred embodiments of the invention as described in the accompanying drawings.

Figure 1:
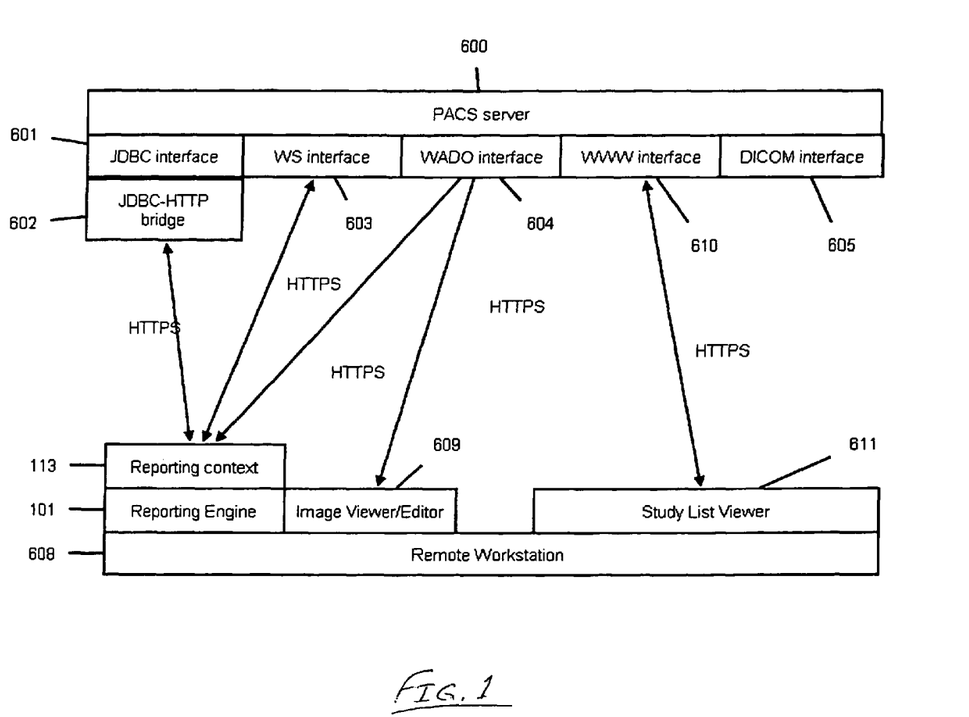
FIG. 1 is a schematic view illustrating a preferred embodiment of a remote reporting and viewing system of the present invention.

FIG. 1 is a schematic view illustrating a preferred embodiment of a remote reporting and viewing system of the present invention. FIG. 1 illustrates a Picture Archiving and Communications System or PACS server 600 with a DICOM interface 605 for communication with imaging modalities. However, this protocol is not normally suitable for the Internet due to firewall issues. For data exchange between a PACS server 600 and a Remote Workstation 608, HTTP protocol is more frequently used. The communication can be encrypted using SSL, and thus HTTPS protocol is used. For downloading images and DICOM structured reports to the remote workstation, standard WADO interface 604 may be used. However, such an interface does not normally provide a way for searching the data and uploading items, such as images modified in workstation, or creating a structured report. For study list viewing and querying, a study list viewer 611 is provided, and in conjunction therewith, a world-wide-web (WWW) interface 610 is most suitable. Another rendition can include a client-side rich client viewer for use as a Web Services interface 603 and a database program that executes structured query languages statements, such as Java Database Connectivity (JDBC) interface 602 tunneled in Secure HTTP (HTTPS protocol), which is designed to transmit individual messages securely. So, in one embodiment, the system comprises:

1. Remote Workstation 608 comprising a Study List Viewer 611 which can be a pure WWW browser, and an Image Viewer/Editor 609 which can be a JAVA Web Start application, or similar software plug-in, so that no manual installation is required, and the software updates can be handled automatically. The Viewer 609 can also include a reporting component which uses a generic Reporting Engine 101 and implements the Reporting Context 113 interfaces, which use the Web Services 603 and the JDBC 602 to communicate with the PACS server 600.

2. PACS server 600 is shown having the following interfaces:
   (1) JDBC 601 tunneled in the HTTPS protocol 602,
   (2) Web services 603,
   (3) WADO 604,
   (4) WWW 610, and
   (5) DICOM 605.

Figure 2:
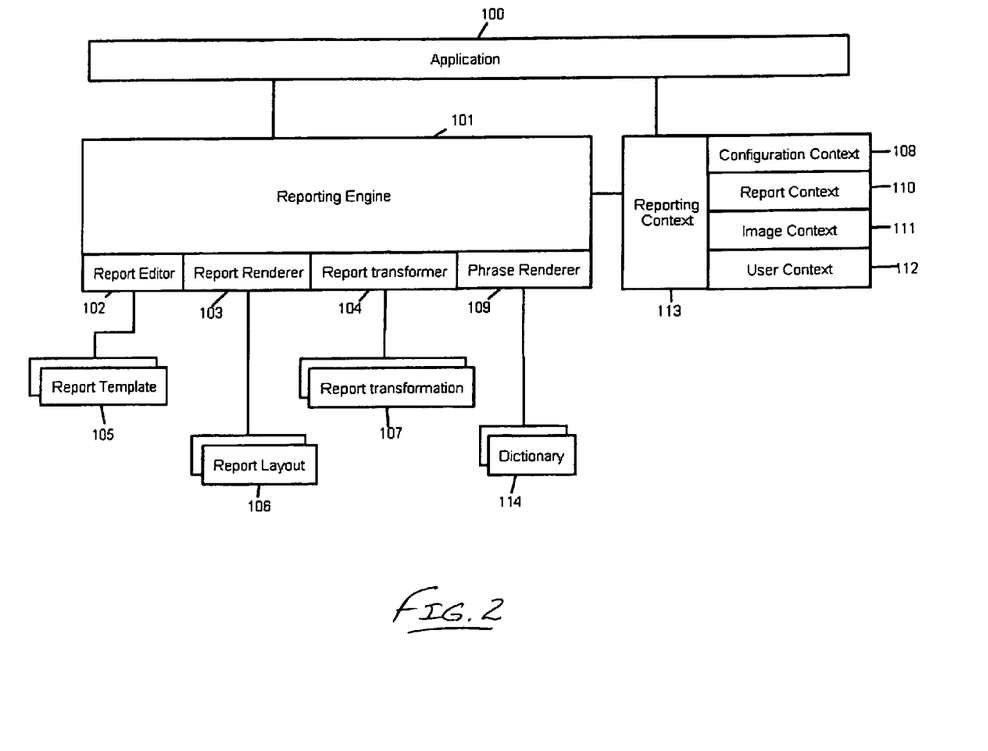
FIG. 2 is a schematic view illustrating a preferred embodiment of the general architecture of a reporting subsystem of the present invention.

FIG. 2 is a schematic view illustrating a preferred embodiment of the general architecture of a reporting subsystem of the present invention. The Reporting Engine 101 connects four classes of components: the Report Editor 102, the Report Renderer 103, the Report Transformer 104 and the Phrase Renderer 109. It can be appreciated by those skilled in the art that the Reporting Engine 101 can work with any number of instances of these classes, further referred to as software plug-ins. The software plug-ins may be developed by the PACS provider or by an independent software vendor (ISV).

The Report Editor 102 is responsible for constructing the Report Editor Graphical User Interface GUI, for parsing the DICOM SR report in order to show it in the Report Editor window and to store the report content created in the GUI to the DICOM SR format. The Reporting Engine 101 can be configured with any number of software plug-ins, so various ways of acquiring user input may be implemented. The current implementation of this software plug-in is based on the DICOM SR pull model (Clunie, David A.; DICOM Structured Reporting; PixelMed Publishing, Bangor, Pa., 2001) which is considered more feasible to control its presentation form, but the Reporting Engine 101 allows for the implementation of push model Report Editor software plug-ins. This novel design does not prevent the present invention from implementing an editor for editing any DICOM SR report in a generic way, such as recognizing a report from a report generated by dictation. The Reporting Engine 101 can provide a way for the software plug-ins to recognize if they are able to open the report or not. This can be done either by software plug-in report introspection or configured in the reporting engine. The Reporting Engine 101 provides a way of configuring the Report Editor 102, so one generic software plug-in may enable multiple Report Templates 105, by configuring the software plug-in. The currently implemented software plug-in can use this possibility to define the report definition and GUI tree in a configuration file. Thus, the Report Template 105 used for the Report Editor 102 can also define the DICOM SR template, explicitly or implicitly.

The Report Renderer 103 is responsible for rendering the report in a format suitable for printing, like a portable document format (PDF). The Reporting Engine 101 provides a way to create configuration files for each Report Renderer 103 software plug-in, so with a generic Report Renderer 103, one may have many Report Layouts 106 that define how the report will appear. The Reporting Engine 101 can be configured with an arbitrary number of Report Renderers 103 and Report Layouts 106. The current implementation is based on Jasper Reports. The precompiled report files as well as the scriptlets are packed into a configuration file that establishes a "report layout." It uses a pull model as it provides more control over how the report will look, but nothing prevents it from implementing a Report Renderer, which can be configured to render any DICOM SR report. The Reporting Engine 101 allows the Report Renderers 103 to determine if they are able to render the report or not. It can be done either by renderer's report introspection or configured in the Reporting Engine.

The Phrase Renderer 109 is designed to assist the Report Renderer 103 in rendering the report. While the main responsibility of the Report Renderer 103 is to generate a report in an external format and define its layout, the Phrase Renderer 109 generates phrases for a given node of a structured report (SR) tree. The phase generation can be recursive so that the whole SR subtree of a given node is converted to a textual representation; or if not, then only the given node is rendered. Phrase generation is always context-based which means that the Phrase Renderer 109 can traverse a full SR tree apart from the node being rendered. The Reporting Engine 101 allows for the storage of configurations for the Phrase Renderer 109, which are shown as Dictionaries 114. In this manner, generic Phrase Renderers 109 can be created; for example, mapping given Xpaths to sentences, which are configurable. Another example of configuration is the precision of numbers, for example, decimal places after comma to display, for given concepts.

The Report Transformer 104 is responsible for converting one DICOM SR report to another, which may be used to create a boilerplate for the final report from a preliminary report, or for scanning a text-based DICOM SR report to create a SR report with one text concept named "findings" and place all the report 330 content in sentences. This report is not "structured" itself but is written in DICOM SR format. An "intelligent" report transformer could convert such a report to a truly structured one. The Reporting Engine 101 provides a way to configure a generic Report Transformer 104 and stores such a configuration as a Report Transformation 107.

In such architecture, three concepts are separated—report definition, which is handled by the Report Editor 102 and stored as Report Templates 105; how a report looks, which is handled by the Report Renderer 103 and stored as the Report Layout 106; and the report vocabulary, which is handled by the Phrase Renderer 109 and configured by the Dictionary 114. In addition to this method, it is possible to have a generic Report Editor 102, Report Renderer 103 and Phrase Renderer 109 that can handle all types of DSR's. The Reporting Engine 101 allows for the creation of more specialized components, to connect each triplet (Report Template 105-Report Layout 106-Dictionary 114) and to store such connected information in configuration by the use of the Reporting Context described further below.

The Application 100, which uses the Reporting Engine 101, can implement a Reporting Context 113 interface that makes it possible for the Reporting Engine 101 components to communicate with the external world. It provides a gateway for storing a report, sending a fax, sending an email, retrieving information about report templates or layouts, and/or retrieving information about current users and their roles. The reporting context can include a configuration context 108, a report context 110, an image context 111, a user context 112, and similar information and capabilities. Through use of this interface, one can use the Reporting Engine 101 in many different environments and with different back-end databases. All that is required to implement this process is the Reporting Context 113, which can be considered as an adapter to connect with external environment.

A PACS lifecycle is counted in years and report definitions may evolve in time. However, it must be a possibility to amend or render older reports despite 360 software evolution. So each reporting software plug-in can be assigned a version to be maintained by the Reporting Engine, and the "lazy-loading" of reporting software plug-ins can be applied. When a viewer is loading, no report plug-ins are loaded, and loading is deferred to the moment of report creation since at this moment it is known which report to create and thus which appropriate report software plug-in would be needed. An alternative to this approach can include "eager loading" as opposed to "lazy loading" which entails loading all reporting software plug-ins together with the viewer, but this is not an efficient method.

Figure 3:
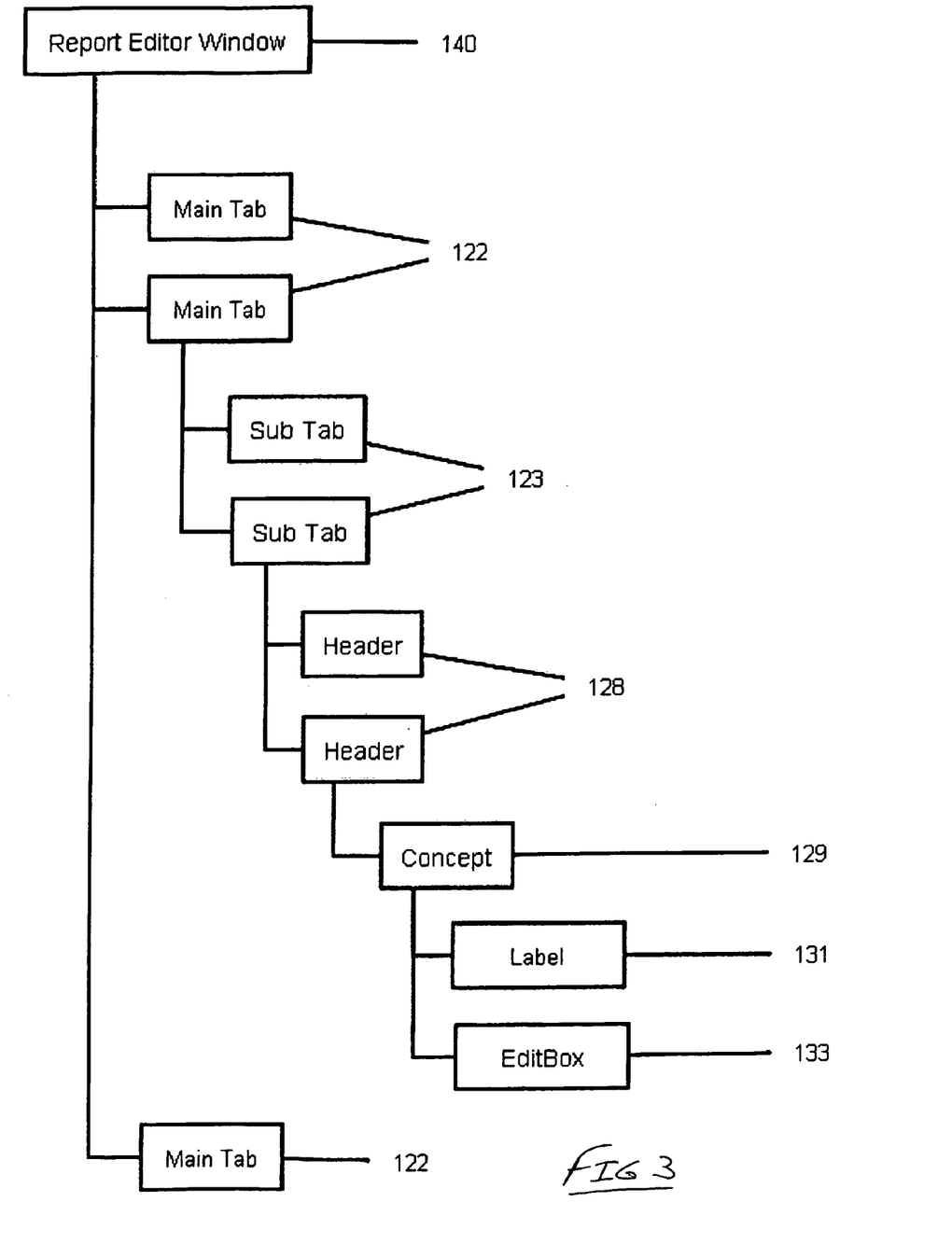
FIG. 3 is a flow chart illustrating a preferred embodiment of a report graphical user interface sample structure of the present invention.

FIG. 3 is a flow chart illustrating a preferred embodiment of a report graphical user interface sample structure of the present invention. FIG. 3 illustrates a Report Editor Window 140 GUI that consists of a set of Main Tabs 122. Each Main Tab 122 can consist of a set of Sub Tabs 123, or similar category delineation. Each Sub Tab 123 consists of a set of Headers 128 and/or measurement tables (125, shown in FIG. 4). A Header 128 defines a group of related Concepts 129. The Header 128 also defines the relation between the Concepts 129, allowing only one concept to be chosen from the set (XOR relation, rendered as radio buttons (XOR—exclusive or) and sample rendition is radio buttons) or any concept to be chosen from the set (OR relation, rendered as checkboxes for example). Each Concept 129 can be rendered as a line in a Header 128 and represent one or several DICOM SR concepts. Concepts can consist of an arbitrary number of GUI components, such as Label 131, EditBox 133, ComboBox 132 (shown in FIG. 4) or SpinEdit 134 (shown in FIG. 4) actions. Comboboxes 132 may be used for either choosing a value (for example, text, numerical or code) from a given set, or to set the coded name of DICOM SR concept represented by the Concept GUI 129. Each concept can add a phrase to the report. This phrase can be displayed in a popup hint-box when the user activates the phrase box (for example, the user moves the mouse arrow over the concept line in the GUI). A Measurement Table 125 (shown in FIG. 4) can provide a convenient way for entering a set of measurements. Each row can represent a single measurement. For example, the table can contain the following columns: measurement name, measurement value, measurement units, default ranges, and image mode. Measurement names and default ranges and optionally the image mode can be fixed in the report definition, while other information is entered by the user. This GUI process allows for presenting and entering the set of values in more lucid fashion than when using Header and Concepts, because the values are aligned into columns. If a value exceeds the default ranges, the whole row can be marked (e.g., colored as red), and a corresponding icon or symbol can be used to signify whether the value exceeds the range or falls below the range.

Figure 4:
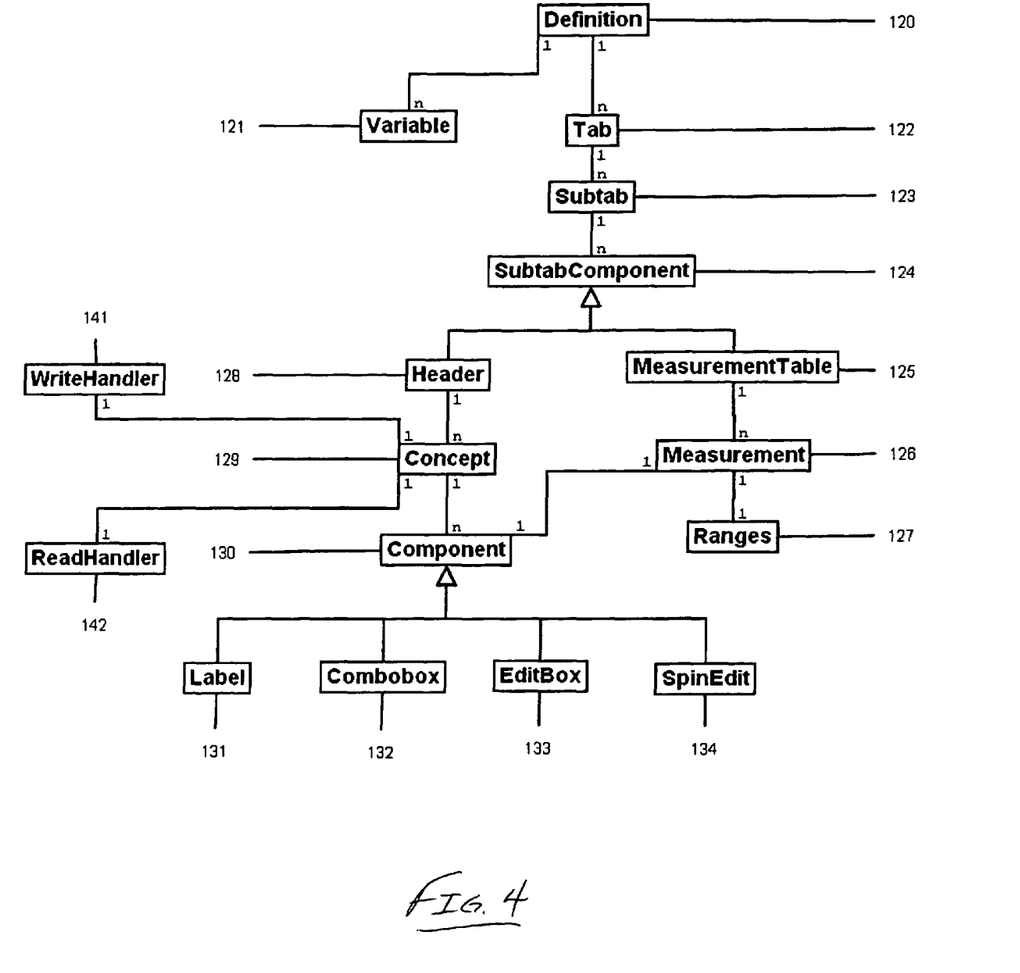
FIG. 4 is a schematic view illustrating a preferred embodiment of a report editor graphical user interface structure of the present invention.

FIG. 4 is a schematic view illustrating a preferred embodiment of a report editor graphical user interface structure of the present invention. In order to create report GUIs as described above, a Generic Report Editor Software Plug-in is developed and illustrated in FIG. 4. This novel method provides a way for creating the GUI definition without hardcoding it in the application. However, if the GUI is not flexible enough, for example, containing a graphical diagram, a custom-developed GUI can be developed and then merged with the definition. The Report Definition 120 is stored as a Report Template 105 (see FIG. 2) and as a configuration for the Report Editor 102 (See FIG. 2). The Report Definition 120 reflects the report GUI, so it can include Tabs 122, which include Sub Tabs 123, such as Subtab Components 124, which can be either a Header 128 or a Measurement Table 125. The Measurement Table 125 is shown including Measurements 126 and Ranges 127. Tabs 122, SubTabs 123 and Headers 128 can have the caption property, and can be hidden without removing them from the Definition 120. A Header 128 can include a set of Concepts 129, and each Concept can include several Components 130, each of which may be a Label 131, a ComboBox 132, an EditBox 133 and/or a SpinEdit 134. Each Concept 129 is also shown having one WriteHandler 141 which is a software component used for storing a DICOM concept corresponding to a GUI Concept 129 and one ReadHandler 142 which is responsible for "pulling" the value out of the source report and populating the GUI Concept. The software architecture permits custom development for providing unique Read/Write Handlers 141, 142 or the use of a default Handler which makes the use of a DICOM Path as described below. The main purpose of Generic Editor Software Plug-in is to provide a GUI, as previously described in the Report Editor GUI, to store SR reports in a given DICOM SR template and read reports created by it. The reading of any SR report, even with a given template, is not a goal for this Generic Editor Software Plug-in, although such an editor can be implemented and deployed in the Reporting Engine 101.

The present invention allows a developer to use Generic Report Editor Software Plug-in "as-is," providing only a suitable report definition, or they may incorporate their own Report Editor Software Plug-in by extending the generic one. This process is accomplished by extending it by:
1. Providing a different tabbed GUI that will be merged with the GUI stored in the definition; This way a GUI with dynamic diagrams may be created;
2. Providing unique Read/Write handlers;
3. Or, modifying the definition and updating the GUI in runtime, which allows for creating tabs dynamically which may be suitable for creating reports like for OB-GYN, where a tab for each fetus may be created.

Figure 5:
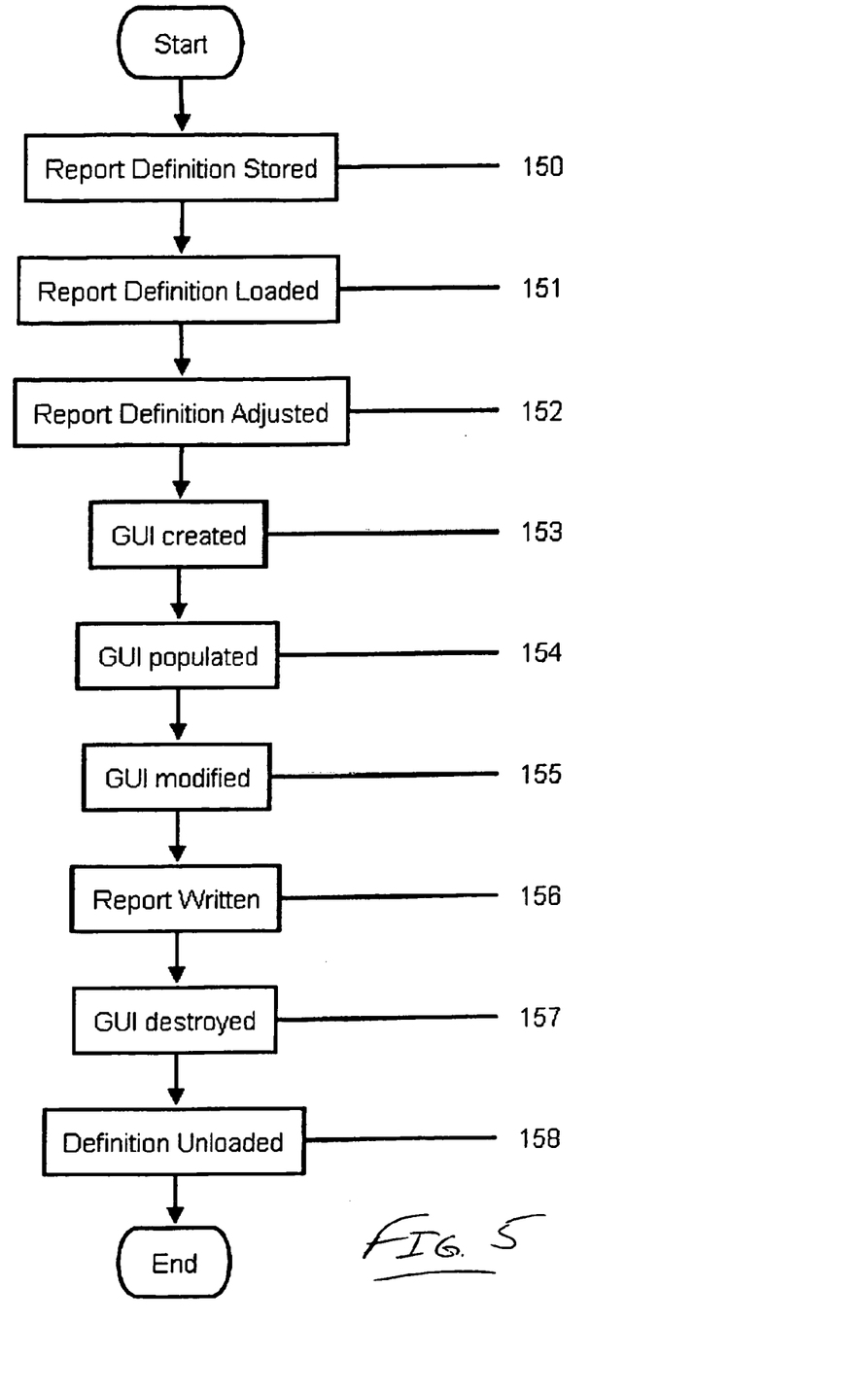
FIG. 5 is a flow chart illustrating a preferred embodiment of a report graphical user interface life cycle function of the present invention.

FIG. 5 is a flow chart illustrating a preferred embodiment of a report graphical user interface life cycle function of the present invention. A report GUI life cycle is depicted in FIG. 5. First, a Report Definition is stored in the Report Engine's configuration 150. Then, when there is need to invoke the Report Editor GUI (for example, when amending or creating a new report), the Report Definition is loaded into memory, e.g., as an interconnected object tree 151. This tree can be further adjusted 152 by providing custom software code, which can change the definition based on the SR object to be amended. Thus, additional tabs/headers may be created, or copied from an existing definition. Following the report definition adjustment 152, the GUI window is created 153 based on the adjusted definition and optionally provided custom GUI. GUI merging is done so each hard-coded tab or subtab is matched to the tab/subtab stored in the definition. Then, the newly created GUI is populated from a source report 154 to set the input fields to the values in the report. The Read Handlers are used to populate the report. The GUI and the definition can be further modified 155 by using a custom code, if needed, from a software report utility functions provided by the Reporting Engine. Thus, for example, a tab for additional fetus may be created on-demand in run-time. When a report is requested to be written, the Write Handlers can be used to store the report in a DICOM SR format 156. The report is then submitted to the PACS using the Reporting Context 110 provided by the application 100. Then the Report Editor GUI is destroyed 157 and the definition is unloaded from the memory 158.

Figure 6:
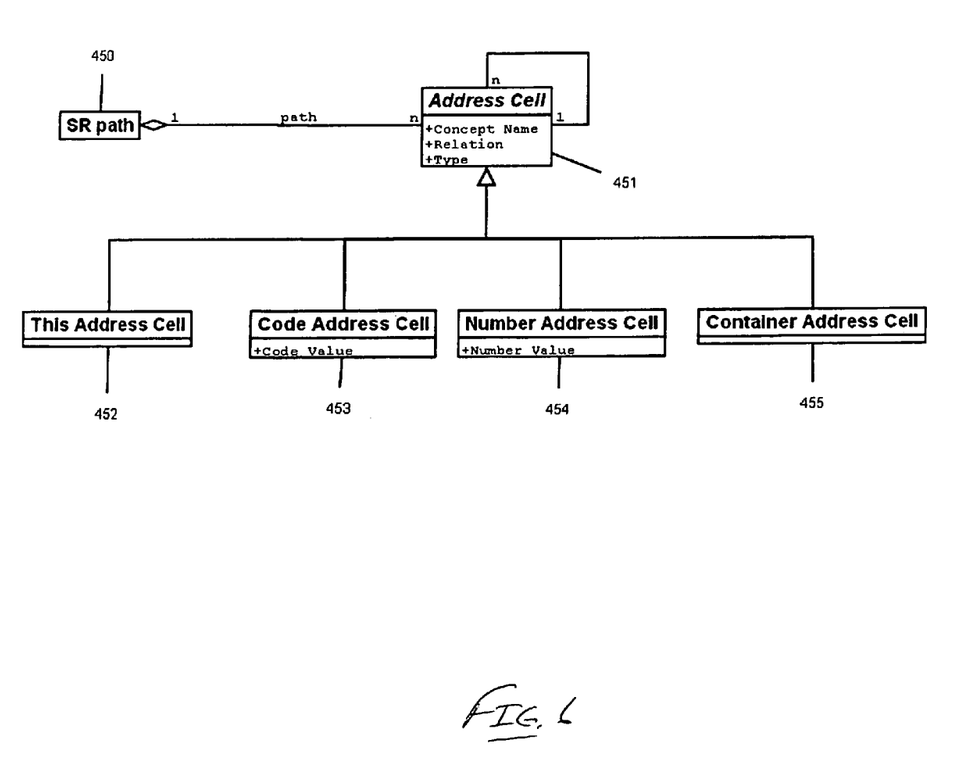
FIG. 6 is a flow chart illustrating a preferred embodiment of a structured reporting path data structure of the present invention.

FIG. 6 is a flow chart illustrating a preferred embodiment of a structured reporting path data structure of the present invention. In FIG. 6, the DICOM SR-path structure is illustrated. The DICOM SR-path is an address of a DICOM SR concept in a SR tree format, which is suitable for retrieving the value of a given concept from the report, but it can also be used to store such values in an appropriate place in the DICOM tree. The DICOM SR-path can be used as a convenient way to describe how the report should be read/stored, and it is used as a default for the Read/Write Handler of the Report Editor described above. It is flexible enough to describe most of the standard DICOM SR templates, and makes it simpler to implement the GUI for report editors as described above.

FIG. 6 depicts a Unified Modeling Language (UML), which is an object modeling and specification language used in software engineering, class diagram of the SR-path. FIG. 6 shows the classes comprising the SR-path data structure and relations between them. The SR-path can also be stored in text format using a language with grammar described with Backus Naur Form (BNF) notation or in Extensible Markup Language (XML) format defined with XML-schema. The SR-path 450 consists of a list of Address Cells 451. Each address cell describes a child of a given node in a SR tree. When finding a concept represented by the last Address Cell instance in the path chain, a set of children is found using each Address Cell instance and the search is performed recursively further. The concept name of each SR node is compared to the concept name attribute of the appropriate Address Cell object, so with the SR type and the SR relation. The classes 452-456 are subclasses of the Address Cell class and they correspond to standard Structured Reports types (not all of them are depicted here). Their values are also compared (when given) during search procedure. Aside from having a simple path from the root of the tree to the searched element, additional criteria may be specified using the 'where' and 'where not' associations in the Address Cell. This association allows for specifying further constraints on the children. A condition is defined by a relative SR-path; evaluation of such SR-path starts from the node currently being processed and if the 'where' path is found—the criterion is fulfilled. In case of 'where not' criterion the condition path has not to be present to satisfy the condition. The conditions are interconnected using an "AND" relation. Below is a sample SR-path, describing a measurement written in conformance with DICOM standard template for Echocardiography procedure report (TID 5200). The SR-path is written in simplified text grammar. The CONTAINER, CODE and NUM keywords are for describing the type of the concepts, slash sign is for advancing to the next child level and bracket signs are for defining constraints. The example is trivialized and simplified because no relationship constraints are shown, human readable names are written instead of DICOM coded terminology and there are no compound or multilevel constraints. An example is illustrated as follows:

CONTAINER(name='Findings')[CODE(name='finding site', value='Left Ventricle'] / CONTAINER (name='Measurement Group')
[CODE (name='Image mode', value='2D')] / NUM(name='LVVOL(d)')
[CODE(name='Method', value='Teichholz')]

To read a measurement using this SR-path, an algorithm would:
1. find a child(ren) of type CONTAINER with concept name 'Findings' having a child of type CODE with concept name 'finding site' and value 'Left Ventricle'
2. for each node found in (1) it should find a child(ren) of type CONTAINER having concept name of 'Measurement Group' having children of type of CODE with concept name "Image mode" and value of "2D"
3. for each node found in (2) it should find a child(ren) of type NUM with concept name 'LVVOL(d)' having a child of type of CODE which has concept name 'method' and the value 'Teichholz'. The NUM node is the measurement being looked for as it is the last item on the path chain.

A similar algorithm is used for writing a value having a given SR-path. For subsequent child levels, it is checked if the level already exists in the SR tree and if not—it is created together with accompanying nodes found in constraints. This is recursively repeated until reaching the last component of the path.

It is crucial that only "equal" and "AND" relations are allowed. Such restriction is necessary for allowing the use of the SR-path for report defining purposes, not only for validation/read purposes. If it allowed "OR" relation, there would be ambiguity during writing process in the moment of writing node constraints. With AND relation, all constraints have to be written to meet the constraint condition, but with OR relation it would make less sense. The same applies when code values, or numeric values are used in the constraints. Only comparisons using 'equal' relation and comparing to constant values are permitted. The concept which location is described using such SR-path can be stored properly in the SR format and all intermediate child nodes will be created. The SR-path can also be used for report transformations (see Report Transformer), and it can also be used with the generic Phrase Renderer for describing the dictionary key. The path is suitable for describing most of the standard SR templates.

SR-path can be parametrized to achieve yet more flexibility. Each Address Cell attribute (and Address Cell's subclasses attributes) can be provided directly—by giving the value of the attribute, or indirectly, by providing only parameter name. Such parametrized SR-path is a more generic template that can be customized at runtime by providing the values of parameters. For write operations all parameter's values must be provided. For read operations some of them may be not provided—in such a case the constraints for searched elements will be loosened, the constraints with values having not present parameter values are treated as not existing ones. Thus the SR-path query may return more results. For each result the parameters not filled before search operation will be filled by the search procedure. Below is example of parametrized SR-path (similar to the previous example)

---

CONTAINER(name='Findings')[CODE(name='finding site', value='Left Ventricle']/CONTAINER(name='Measurement Group')[CODE(name='Image mode', value=':mode')]/NUM(name='LVVOL(d)')[CODE(name='Method', value=':method')]

---

The parameters are written here as the colon sign followed by the parameter name. For write operations all parameter values have to be provided. So it can be set that parameter 'mode' has a value of '2D' and parameter 'method' has the value of 'Teichholz'. For read operations two cases are possible: all parameter values are provided (to 2D and Techholz respectively for the sake of the example); this way the LVVOL(d) done with 2D and Teicholz method is retrieved. Actually more than one result may be returned if there is more LVVOL(d) parameters existing in the report.

Some (or all) values for parameters are not provided. For example value for parameter 'image mode' is provided and value for parameter 'method' is not given; in this case multiple results will be returned for any LVVOL(d) done with 2D, and the return parameter 'method' will be filled in with appropriate method for each result. With given search result is associated a set of names of return parameters, and with each parameter name is associated a set of parameter values. This way it is possible to retrieve set of 'method' parameter values if there were more than one method modifier attached one LVVOL(d) measurement (such example makes no practical sense, but the ability of getting set of parameter values is needed for general case)

Another example of employing parameters in searches is to retrieve numeric values with return parameters. The following SR-path snippet shows this:

'NUM(name='*LVVOL(d)*', value=':value' units=':units')'

This makes sense only if there is only one result matching the SR-path, or only one units of measurement is used for particular parameter. If not—a set of values and other set of units will be returned and there will be no way of connecting them. In such a case, using return parameters for getting the values is not advised. Processing node associated with each search result to retrieve value and unit of measurement should be applied.

The SR-path class 450 represents only a stored definition of an SR-path. It can be stored in any format or build in runtime. For actual find/write operations SR path runtime interface 457 is used. Instances of sample class implementing this interface—SRDocumentPath 459 are created for each SR path definition and structured report instance (represented here by SRDocument 458 interface). Apart from providing operations for finding, writing and deleting nodes, the SR path runtime interface has the operations to manage set of input parameters in runtime, needed for operations. Find operations can be applied to the root of the structured report (so the path is considered non-relative) as well as to other node in this report (so the path is considered relative). The same is true for delete and write operations. Write operation can work in three modes corresponding to behavior in case of finding node matching to the path already in the report. The write operation can:

fail if node described by path already exists
overwrite the existing one
create a sibling to the existing one
The delete operation can work in two modes:
delete only the node found in the path
delete also all preceding nodes in path if there are no other sibling nodes left in the report being worked on, on each respective level. For example path:

---

CONTAINER(name='Findings')[CODE(name='finding site', value='Left Ventricle']/CONTAINER(name='Measurement Group')[CODE(name='Image mode', value='2D')]/NUM(name='LVVOL(d)')[CODE(name='Method', value='Teichholz')]

---

The delete operation will first delete the last NUM item (if found). Then it will check if there is any child of Measurement Group node left—if not it will delete also the 'Measurement group' container. Then it will check if there is any child of Findings node left—if not it will delete also the Findings container node. For delete operations, all parameter values must be provided.

In the DSR processing application there are several data work-flows involved. Data (for example, measurement values) should be transmitted seamlessly from the procedure report generated by the modality or OCR engine, through the preliminary report to the final report. Each of these reports may and usually will have different structure. So, a way of converting a report from one form to another is provided.

Figure 7:
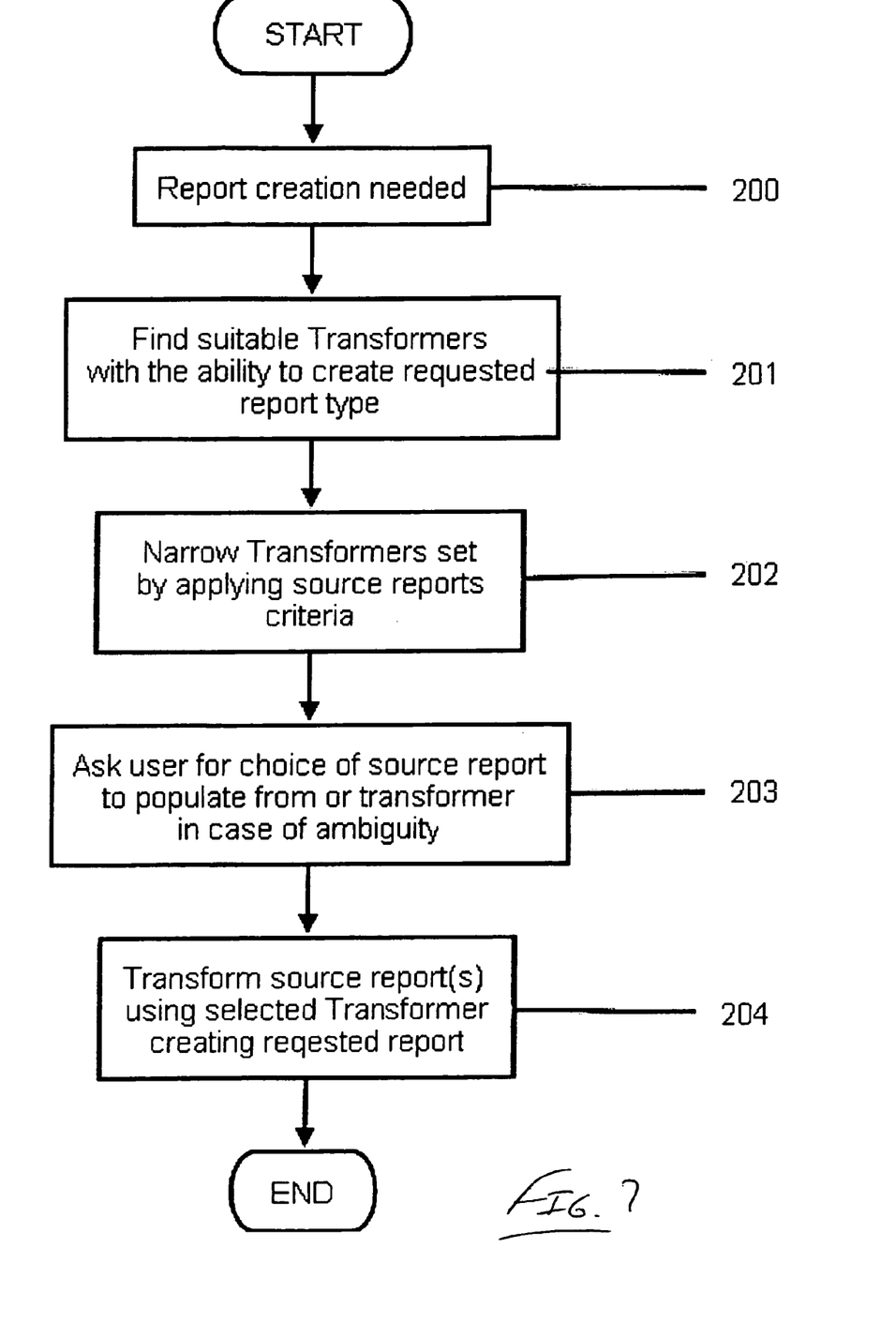
FIG. 7 is a flow chart illustrating a preferred embodiment of a report transforming algorithm of the present invention.

FIG. 7 is a flow chart illustrating a preferred embodiment of a report transforming algorithm of the present invention. The transformer processing algorithm as used in the Reporting Engine is depicted in FIG. 7. When report creation of a given template is needed 200, the Reporting Engine searches for the transformation that could produce the desired report 201. Each Transformer 104 software plug-in is capable of determining the output report template it creates. Then, the reporting engine "asks" each selected transformer for the ability of performing transformation on a given set of already existing SR reports. Only transformers able to proceed with the given input data are selected 202. The set of possible transformations may be ambiguous (for example, having multiple preliminary reports yet the transformer allows the selection to convert one preliminary report to one final report). In such a case, the user is requested to choose the appropriate transformation 203. The transformation is performed 204 and the Report Editor Software Plug-in makes the conversion. In case of finding no suitable report transformations, a new report is created by the Report Editor Software Plug-in.

FIG. 7 illustrates an example of a Generic Report Transformer. In this embodiment, the Generic Report Transformer would convert a SR report to XML document format, then apply an Extensible Style Language Transformation (XSLT), stored in the transformer configuration, and then convert back to the resulting XML document to SR format. However, another approach is more convenient with the use of SR-paths. In such an embodiment, a transformer is provided with two lists of SR-paths—one source list and one destination list. Each element from the destination list corresponds to one element in the source list. When transforming a report, each pair source value is found in the source report using source SR-path and then written in the destination report using destination SR-path. This may be shown on the following example. The transformer is given 2 lists; source: (A/B, C/D) and destination (Q/W, X/Z). When it processes a report with single concept A/B—it will be transformed to report Q/W. The rule C/D->X/Z would not be launched because the report does not contain a C/D branch. Had the report contained some other branch, like for example T/Y/U, it would be discarded, because there is no rule for processing it. It should be noted that SR-paths can describe whole sub-tress as well as single measurements, so whole branches of the source tree can be easily copied, working 655 as a form of a 'push' transformation. However this processing differs from XSLT pattern based transform, and it is more convenient for working with DICOM Structured Reports and copying selected measurements. XSLT is more powerful and generic but it is harder to provide a SR transformation definition with this and the transformation definition is a mess. Additionally, such a report transformer has an SR document which acts as a template for the resulting report. It has a SR tree with some predefined branches already in it, to make it easier to create transforms. The concepts populated from source reports are merged into this predefined 'skeleton' report.

Figure 8:
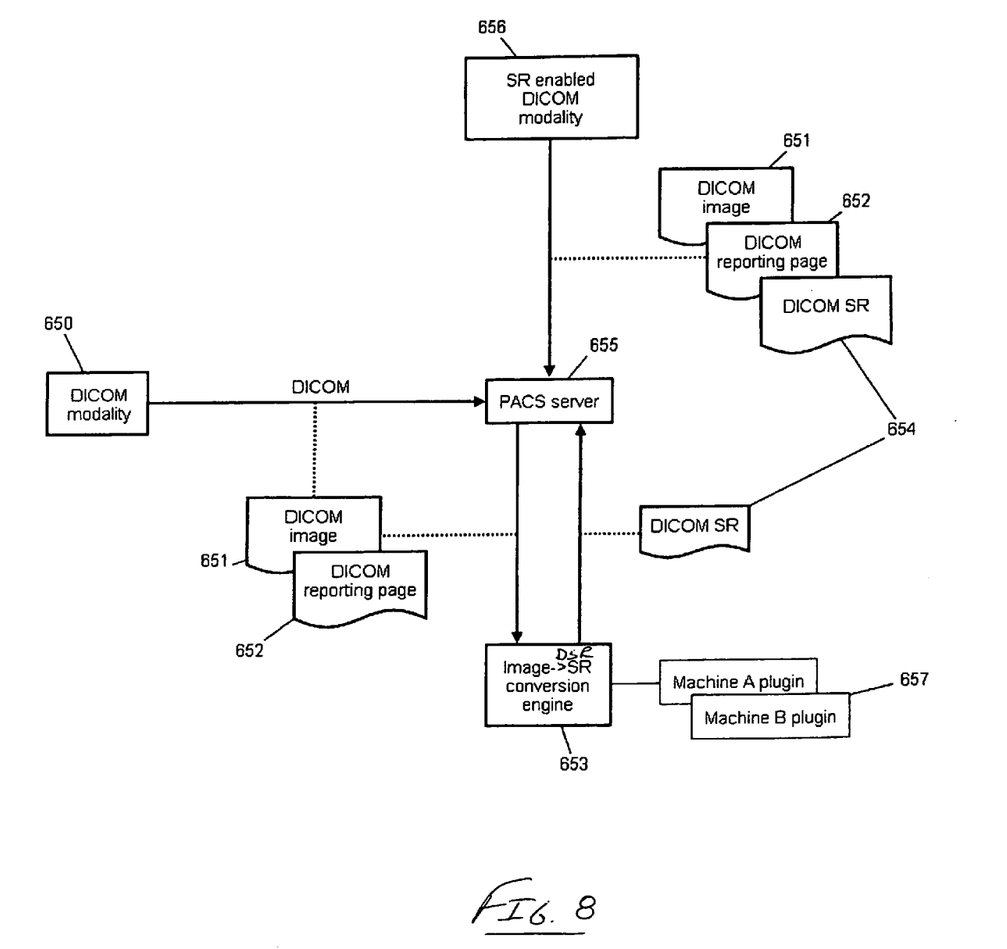
FIG. 8 is a flow chart illustrating a preferred embodiment of a report transforming algorithm of the present invention.

FIG. 8 is a flow chart illustrating a preferred embodiment of a report transforming algorithm of the present invention. FIG. 8 illustrates an Image to DICOM Structured Report (DSR) conversion engine. In the illustrated preferred embodiment, the Report Transformer 104 processes source DICOM structured reports and produces output structured reports which can be further modified using the Report Editor 102. It makes it possible to populate measurements from a procedure report to the final report or populate certain data stored by the technician in the preliminary report to the final report. In order to have it working, the source reports have to be in DICOM SR format, and this works well when source modality has the ability to produce such reports. In the embodiment in FIG. 8, the SR enabled DICOM modality 656 sends DICOM images 651 together with optional DICOM reporting pages 652 and DICOM SR reports 654 to the PACS server 655. Some imaging modalities, for example, ultrasound machines, like the Philips Sonos 5500, Philips HDI 5000, Siemens Acuson and Siemens Sequoia 650, however, do not support outputting measurement values in DSR format—this pertains mainly for older devices. They send only DICOM images and DICOM reporting pages with measurements stored in bitmap format. This format is not suitable for reading by machines, so the claimed Image to SR conversion engine provides a format conversion from bitmap format to DICOM Structured Reports. So when a PACS server 655 receives a study from the modality it stores it and forwards to the Image to DSR conversion engine 653. The conversion engine 653 may be implemented as a standalone DICOM entity and as such may accept input images using DICOM protocol, or may be just an internal part of the PACS server, or may fetch the source images from a WADO server given the set of links—the actual deployment is not a subject of this claim. Since OCR algorithm depends highly on the layout of the source images, and thus on the modality vendor, several plug-ins 657 may be deployed in the Conversion Engine 653, each for converting images coming from another type of the modality. The Conversion Engine 653 performs the following steps:

(1) Asks each OCR plug-in if it can handle the study. The OCR plug-in is free on how to implement this check; the easiest way is to check for appropriate DICOM tags, but it may use image recognition at this point.
(2) For each image, the selected plug-in checks to determine if the image contain measurement data. It may choose only report pages, or other images as well for further analysis.
(3) Having a set of suitable images, the OCR engine delegates OCR work for a selected plug-in, which is supposed to produce a set of DSR reports.
(4) The OCR engine sends produced reports back to the PACS server When implementing the OCR plug-in a developer can make use of a standard library shared by the Conversion Engine 653 which makes it easier to perform image segmentation and font management. Since the native language for implementing such plug-ins is JAVA, the plug-in may use Java Advanced Imaging libraries, however nothings prevents implementing such plug-in in native CPU code.

It is important that the software plug-in should produce one of the standard DICOM SR template like, for example, TID 5200 for Ultrasound Adult Echo Procedure Reports, because there will be no need to write additional code in the Report Transformer which can handle standard DICOM SR templates.

Figure 9:
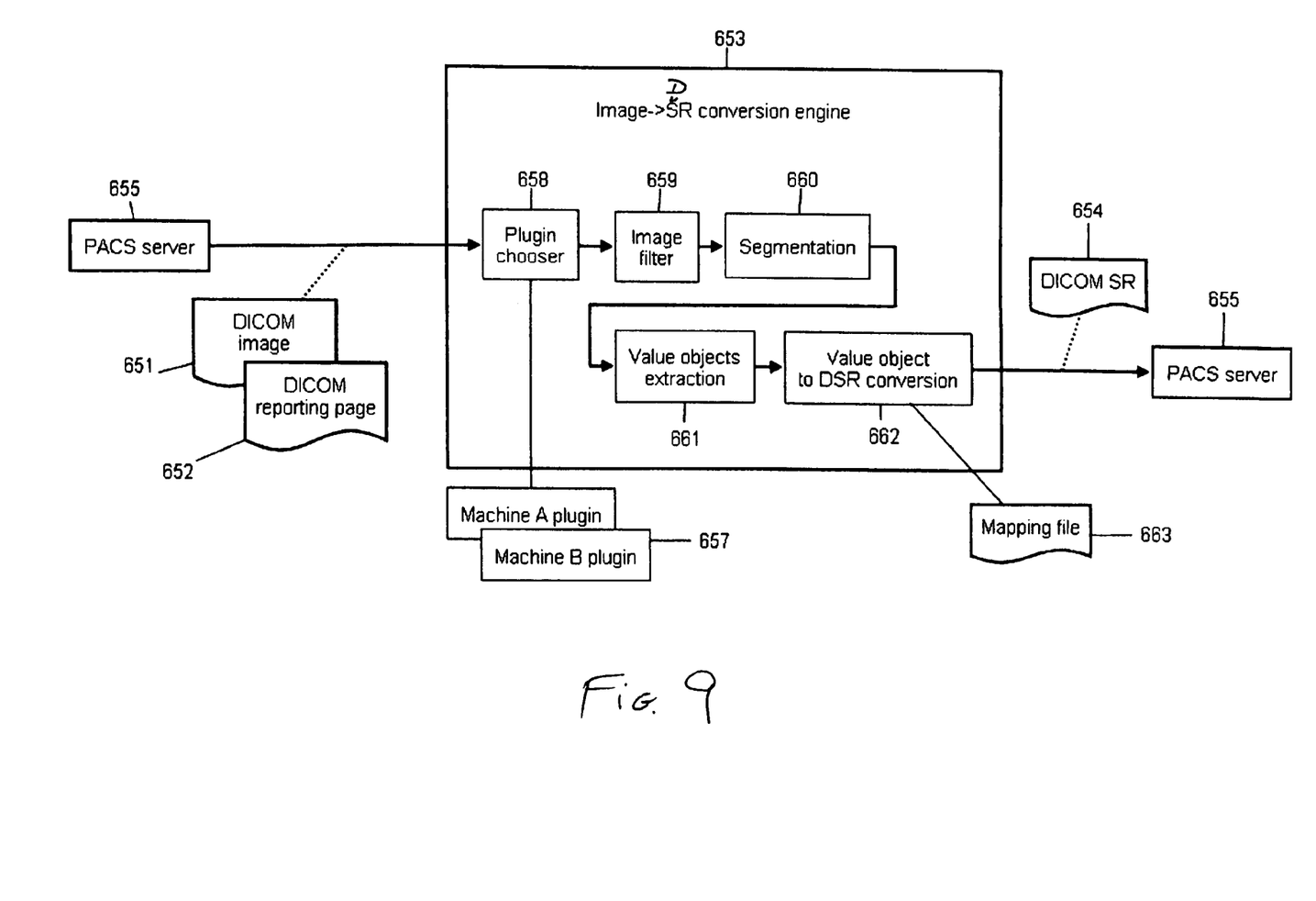
FIG. 9 is a flow chart illustrating a preferred embodiment of an Image to DICOM Structured Report (DSR) conversion engine of the present invention.

FIG. 9 illustrates an Image to DICOM Structured Report (DSR) conversion 715 engine. In this preferred embodiment the Report Transformer 104 processes source DICOM structured reports and produces output structured reports that can be further modified using Report Editor 102. It makes it possible to populate measurements from a procedure report to the final report or populate certain data stored by the technician in the preliminary report to the final report. In order to have it working the source reports have to be in DICOM SR format, and this works well when source modality has the ability to produce such reports. In such embodiment SR enabled DICOM modality 656 sends DICOM images 651 together with optional DICOM reporting pages 652 and DICOM SR report(s) 654 to the PACS server 655. Some imaging modalities (example, ultrasound machines, like the Philips Sonos 5500, Philips HDI 5000, Siemens Acuson and Siemens Sequoia) 650 however don't support outputting measurement values in DSR format—this pertains mainly for older devices. They send only DICOM images and DICOM reporting pages with measurements stored in bitmap format. This format is not suitable for reading by machines, so the claimed Image to SR conversion engine provides a format conversion from bitmap format to DICOM Structured Reports. So when a PACS server 655 receives a study from the modality it stores it and forwards to the Image to DSR conversion engine 653. The conversion engine may be implemented as a standalone DICOM entity and as such may accept input images using DICOM protocol, or may be just internal part of the PACS server, or may fetch the source images from WADO server given the set of links—the actual deployment is not a subject of this claim. Since OCR algorithm depends highly on the layout of the source images (and thus on the modality vendor), several plug-ins 657 may be deployed in the Conversion Engine, each for converting images coming from another type of the modality. The Conversion Engine performs the following steps (see FIG. 9):

1. Asks each OCR plug-in if it can handle the study 658. The OCR plug-in is free how to implement this check; the easiest way is to check for appropriate DICOM tags, but it may use image recognition at this point
2. For each image the selected plug-in checks if the image contain measurement data 659. It may choose only report pages, or other images as well for further analysis.
3. Having a set of suitable images, OCR engine delegates OCR work for selected plug-in, which is supposed to produce a set of DSR reports. The Conversion engine publishes a library which makes it easier to implement the most typical OCR processing. Such steps are presented below:
    3.1. The frame is divided onto segments in segmentation process 660. Segments are hierarchical, which corresponds to the most commonly met case where for example header segments are related or contain subheader segments and/or measurements segment, and a measurement segment contains a label segment, value segment and a units of measurement segment. The library makes it easier to do segmentation because it contains several segmentation routines and publishes a set of standard segment classes.
    3.2. The value object extraction is performed 661. The library provides support for character recognition based on a font database (appropriate set of glyphs is provided by the plug-in). It also provides a standard value object classes for headers (which may contain other headers and/or measurements) and measurement value objects (which contain a label, value and a unit of measurement)
    3.3. The conversion of value object to DICOM Structured Report is performed 662. If a plugin uses standard value objects, this step may be performed entirely by the Conversion Engine. If so—it uses an external configuration mapping file 663 which maps a native modality measurement (in context of headers and/or subheaders it is located in) into a SR-path.
4. The OCR engine sends produced reports to a PACS server. It can be configured to sent it back to the server that sent the study.

Thus, in an embodiment, the conversion engine can perform data recognition on input DICOM files to produce a structured clinical report by identifying DICOM files that contain measurement data, report pages, and/or images, extracting portions of preselected DICOM images that contain information to be extracted and converted, performing value object extraction on the portions (which can involve OCR when extracting data from bitmap images or reporting pages), and converting the value objects to a standard DICOM structured report format.

When implementing the OCR plug-in a developer can make use of a standard library shared by Conversion Engine which makes it easier to perform image segmentation and font management. Since the native language for implementing such plug-ins is JAVA, the plug-in may use Java Advanced Imaging libraries, however nothings prevents implementing such plug-in in native CPU code.

It is important that the software plug-in should produce one of the standard DICOM SR template (like TID 5200 for Ultrasound Adult Echo Procedure Reports), because there will be no need to write additional code in Report Transformer which can handle standard DICOM SR templates. In such a case the OCR engine can be also used as a standalone box for converting images to standard DICOM Structured reports so other vendors may populate the values from non DSR enabled modalities, without the need of implementing OCR processing by themselves.

The invention being thus disclosed and illustrative embodiments depicted 800 herein, further variations and modifications of the invention will occur to those skilled in the art. All such variations and modifications are considered to be within the scope of the invention, as defined by the claims appended hereto and equivalents thereof.

Additional advantages and modification will readily occur to those skilled 805 in the art. The invention in its broader aspects is therefore not limited to the specific details, representative apparatus, and the illustrative examples shown and described herein. Accordingly, the departures may be made from the details without departing from the spirit or scope of the disclosed general inventive concept.

What is claimed is:

1. A method for implementing a structured clinical reporting system over the Internet, the structured clinical report having a DICOM Structured Reporting format, and the Internet adapted to work in conjunction with hypertext transfer protocol (HTTP) for connecting a server and multiple workstations via the Internet, the method comprising the steps of:
    (a) providing communication between a workstation and the server via the Internet;
    (b) providing a reporting engine in operative communication with the workstation, an image viewer-editor, and the server;
    (c) using the workstation to create the structured clinical report, sign the structured clinical report, render the structured clinical report, transmit the structured clinical report to and from the server, or combinations thereof;
    (d) using a conversion engine to perform data recognition on input files to produce the structured clinical report using a plurality of software plug-ins that identify a plurality of data comprising: modality; vendor; DICOM tags; DICOM structured report data comprising partial, incomplete, or non-standard reports; DICOM data; images; or combinations thereof, wherein performing the data recognition comprises:
        determining whether the plurality of software plug-ins include at least one plug-in usable to perform value object extraction on one or more files;
        receiving input files which contain measurement data, report pages, images, DICOM Structured Report data, DICOM data, or combinations thereof;
        using said at least one plug-in to extract a data structure from the input files;
        extracting portions segments of preselected images, or DICOM data from the input files which contain information to be extracted and converted;
        performing value object extraction on the segments portions to form value objects; and
        determining a structured report template to be created and converting the value objects and the data structure to a standard DICOM Structured Report format;

providing a reporting engine in communication with the conversion engine, wherein the reporting engine comprises a report transformer having a plurality of transformations;

searching the plurality of transformations to determine at least one transformation usable to produce a structured report from the standard DICOM Structured Report format;

permitting selection of said at least one transformation by a user, thereby defining a requested report type; and creating the requested report type from said at least one transformation, forming a report with autopopulated values;

(e) providing a picture archiving and communications system (PACS) server, in communication with a database server, a viewer, and the workstation and transmitting the value objects to the PACS server;

(f) providing communication between the PACS server and an imaging modality using a DICOM interface, such that the PACS server is in operative communication with imaging modalities via a DICOM protocol and is in operative communication with the database, whereby the workstation and the conversion engine are in operative communication with the PACS server via the Internet using the HTTP protocol.

2. The method of claim 1, wherein the image viewer-editor is a DICOM viewer having rich client characteristics.

3. The method of claim 1, wherein the workstation provides the automatic downloading, installing and running of the rich-client viewer.

4. The method of claim 1, wherein the image viewer-editor is a rich client capable of being installed remotely.

5. The method of claim 1, wherein the image viewer-editor is a DICOM viewer automatically downloaded and installed.

6. The method of claim 1, wherein the conversion engine is implemented in WWW-based, thin-client technology.

7. The method of claim 1, wherein the conversion engine comprises a study list comprising a graphical user interface for displaying patient exams, studies and information listed by category including chronological order, patient name, study creation date, accession number, study status with preliminary report completed, study status with final report completed, study status without any report and combinations thereof.

8. The method of claim 1, wherein access to the database is from a remote workstation to the PACS server such that database traffic between the remote workstation and the database server is tunneled over secure HTTP protocol.

9. The method of claim 1, wherein a DICOM object is downloaded from the PACS server to the interface viewer using WADO protocol.

10. The method of claim 1, further comprising Web Services for providing communication between the PACS server and a client-side, rich-client viewer.

11. The method of claim 1, wherein the workstation is a computer.

12. The method of claim 1, wherein the workstation comprises a central processor unit and a random access memory.

13. The method of claim 1, wherein the picture archive communication systems (PACS) comprises a central data storage device.

14. The method of claim 1, wherein the clinical reports are stored and transmitted using a DICOM Structured Report format.

15. The method of claim 1, wherein the step of performing value object extraction on the segments to form value objects further comprises implementing algorithms to perform value object extraction on the segments to form value objects for extracting data from bitmap images, reporting pages, DICOM data, or a combination thereof further comprises performing optical character recognition.

16. The method of claim 1, wherein the conversion engine is implemented as a standalone DICOM entity.

17. The method of claim 1, wherein the conversion engine is implemented as part of a server.

* * * * *